United States Patent [19]
Kraska

[11] 4,291,060
[45] Sep. 22, 1981

[54] COMPOUNDS DERIVED FROM FORMYLPHENOXYACETIC ACID AS ANTIVIRAL AGENTS IN ANIMALS

[75] Inventor: Allen R. Kraska, East Lyme, Conn.

[73] Assignee: Pfizer Inc., New York, N.Y.

[21] Appl. No.: 9,288

[22] Filed: Feb. 5, 1979

Related U.S. Application Data

[63] Continuation-in-part of Ser. No. 933,958, Aug. 15, 1978, abandoned.

[51] Int. Cl.³ .................... A01N 37/30; A01N 37/18; C07C 103/28; C07C 93/06
[52] U.S. Cl. .............................. 424/316; 260/501.17; 260/501.19; 424/324; 424/330; 564/142; 564/164; 564/175; 564/347; 564/354
[58] Field of Search .................... 260/570.7 R, 559 A; 424/316, 324, 330; 564/164, 347, 354

[56] References Cited

U.S. PATENT DOCUMENTS

| | | | |
|---|---|---|---|
| 3,047,628 | 7/1962 | Goldberg et al. | 260/570.7 |
| 3,732,299 | 5/1973 | Levine et al. | 260/558 |
| 3,960,958 | 6/1976 | Richardson | 260/570.7 X |
| 4,001,322 | 1/1977 | Marshall | 260/570.8 X |
| 4,064,125 | 12/1977 | Krapcho | 260/570.7 X |

Primary Examiner—Robert V. Hines
Attorney, Agent, or Firm—Connolly and Hutz

[57] ABSTRACT

Novel compounds derived from formylphenoxyacetic acid such as N,N-dihexadecyl-4-(aminomethyl)phenoxy acetamide and N,N-dihexacecyl-2-(4-(aminomethyl)-phenoxy) ethylamine and their non-toxic acid addition salts are useful for combating viral infections in vertebrate animals.

12 Claims, No Drawings

COMPOUNDS DERIVED FROM FORMYLPHENOXYACETIC ACID AS ANTIVIRAL AGENTS IN ANIMALS

CROSS-REFERENCE TO RELATED APPLICATIONS

This application is a continuation-in-part of U.S. patent application Ser. No. 933,958, filed Aug. 15, 1978 and now abandoned.

BACKGROUND OF THE INVENTION

Virus infections which attack animals, including man, are normally contagious afflictions which are capable of causing great human suffering and economic loss. Unfortunately, the discovery of antiviral compounds is far more complicated and difficult than the discovery of antibacterial and antifungal agents. This is due, in part, to the close structural similarity of viruses and the structure of certain essential cellular components such as ribonucleic and deoxyribonucleic acids. Nevertheless, numerous non-viral "antiviral agents", i.e. substances "which can produce either a protective or therapeutic effect to the clear detectable advantage of the virus infected host, or any material that can significantly enhance antibody formation, improve antibody activity, improve nonspecific resistance, speed convalescence or depress symptoms" [Herrman et al., Proc. Soc. Exptl. Biol. Med., 103, 625 (1960)], have been described in the literature. The list of reported antiviral agents includes, to name a few, interferon and synthetic materials guanidine, pteridines and methisazone. Because of the rather narrow range of viral infections that can be treated by each of the antiviral agents commercially available at the present time, new synthetic antiviral agents are always welcomed as potentially valuable additions to the armamentarium of medical technology.

SUMMARY OF THE INVENTION

It has now been found that certain novel compounds derived from formylphenoxyacetic acid are capable of combating viral infections in vertebrate animals. The novel compounds of this invention have the formula

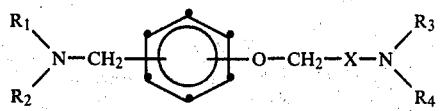

and the non-toxic acid addition salts thereof wherein
$R_1$ is hydrogen, lower alkyl or lower hydroxyalkyl;
$R_2$ is hydrogen or lower hydroxyalkyl;
$R_3$ is hydrocarbyl containing 12 to 20 carbon atoms;
$R_4$ is hydrocarbyl containing 12 to 20 carbon atoms; and
X is —CO— or —CH$_2$—.

The invention disclosed herein comprises the novel antiviral compounds of formula I and the novel method of treating viral infections in vertebrate animals characterized by administration of a pharmaceutical composition containing an antivirally effective amount of a compound of formula I as the essential active ingredient.

DETAILED DESCRIPTION OF THE INVENTION

The compounds of formula I exhibit prophylactic antiviral activity in vivo in vertebrate animals. It is probable that these compounds function as antiviral agents by virtue of their ability to induce the production of endogenous interferon, although the present invention is not to be construed as limited by such a theory.

By "non-toxic" acid addition salts is meant those salts which are non-toxic at the dosages administered. The non-toxic acid addition salts which may be employed include such water-soluble and water-insoluble salts as the hydrochloride, dihydrochloride, hydrobromide, phosphate, diphosphate, nitrate, sulfate, acetate, hexafluorophosphate, citrate, gluconate, benzoate, propionate, butyrate, sulfosalicylate, maleate, laurate, malate, fumurate, succinate, oxalate, tartrate, amsonate (4,4'-diaminostilbene-2,3'-disulfonate), pamoate (1,1'-methylene-bis-2-hydroxy-3-naphthoate), stearate, 3-hydroxy-2-naphthoate, p-toluenesulfonate, methanesulfonate, lactate, dilactate, and suramin salts.

A preferred group of the compounds of formula I consists of the hydrochloride, dihydrochloride, hydrobromide, dihydrobromide, phosphate, diphosphate, lactate, methanesulfonate and succinate salts of the bases of formula I.

The compounds of this invention are prepared according to the following scheme:

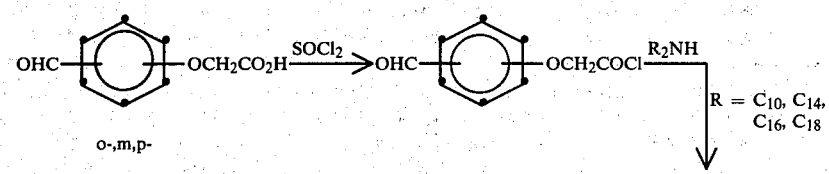

-continued

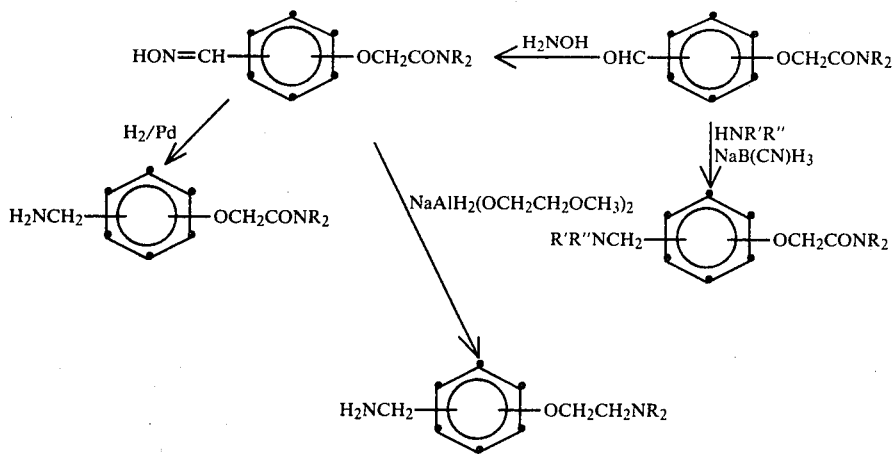

An interesting result has been observed when thionyl chloride is reacted with the isomeric formylphenoxyacetic acids. The meta isomer is smoothly converted to the aldehyde acid chloride. The ortho and para isomers give the expected acid chloride; however, the aldehyde group is converted to a dichloromethyl group in the process as shown in the following equation:

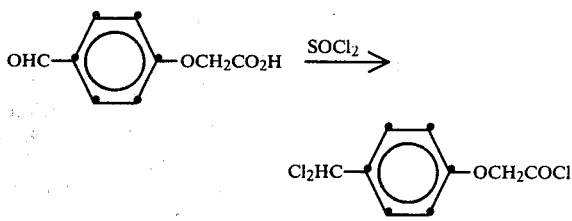

Acid addition salts of the bases of formula I may be prepared by conventional procedures such as by mixing the base compound in a suitable solvent with the required acid and recovering the salt by evaporation or by precipitation upon adding a non-solvent for the salt. Hydrochloride salts may readily be prepared by passing dry hydrogen chloride through a solution of the base compound in an organic solvent.

The antiviral activity of the compounds of formula I is determined by the following procedure. The test compound is administered to mice by the intraperitoneal route eighteen to twenty-four hours prior to challenging them with a lethal dose of encephalomyocarditis (EMC) virus. The survival rate is determined ten days after challenge and an ED$_{50}$ [dosage level (mg of compound/kg body weight) required to obtain a fifty percent survival rate] calculated. The procedure in which the drug is given eighteen to twenty-four hours before, and at a distinctly different site from, virus injection is designed to eliminate local effects between drug and virus and identify only those compounds which produce a systemic antiviral response.

Antiviral activity is expressed as the relative survival ($S_r$) in experimental groups compared to the controls on the tenth day after challenge. $S_r$ is defined by the formula $$S_r = \left[\frac{S_x + \sum_{i=1 \text{ to } 10} x_i - \sum_{i=1 \text{ to } 10} e_i}{100 + 100 - \sum_{i=1 \text{ to } 10} e_i}\right] \times 100$$

wherein
$S_r$ = relative survival
$S_x$ = percent survival after ten days in experimental group
$x_i$ = number of survivors on the ith day in experimental group
$e_i$ = number of survivors on the ith day in control group The ED$_{50}$ [dosage level (mg of compound/kg or body weight) required to obtain a fifty percent survival rate] can be determined graphically by plotting $S_r$ (ordinate) vs. 1 n dosage level (abscissa) and then fitting the points with a line of predetermined slope by least squares. The dosage level at which this fitted line has an ordinate of 50 is equivalent to the ED$_{50}$.

Certain of the compounds of formula I were also tested for their ability to induce circulating interferon in mice after parenteral administration, using the procedure described by Hoffman, W. W. et al., Antimicrocial Agents and Chemotherapy, 3, 498–501 (1973).

Parenteral, topical and intranasal administration of the above-described compounds to an animal before exposure of the animal to an infectious virus provide rapid resistance to the virus. Such administration is effective when given as much as five days prior to exposure to the virus. Preferably, however, administration should take place from about three days to about one day before exposure to the virus, although this will vary somewhat with the particular animal species and the particular infectious virus.

When administered parenterally (subcutaneously, intramuscularly, intraperitoneally) the materials of this invention are used at a level of from about 1 mg/kg of body weight to about 250 mg/kg body weight. The favored range is from about 5 mg/kg to about 100 mg/kg of body weight, and the preferred range from about 5 mg to about 50 mg/kg of body weight. The dosage, of course, is dependent upon the animal being treated and the particular compound involved and is to be determined by the individual responsible for its administration. Generally, small doses will be administered initially with gradual increase in dosage until the optimal dosage level is determined for the particular subject under treatment.

Vehicles suitable for parenteral injection may be either aqueous such as water, isotonic saline, isotonic dextrose, Ringer's solution, or non-aqueous such as fatty oils of vegetable origin (cottonseed, peanut oil, corn, sesame) and other non-aqueous vehicles which will not interfere with the efficacy of the preparation and are non-toxic in the volume or proportion used (glycerol, ethanol, propylene glycol, sorbitol). Additionally, compositions suitable for extemporaneous preparation of solutions prior to administration may advantageously be made. Such compositions may include liquid diluents, for example, propylene glycol, diethyl carbonate, glycerol, sorbitol.

When the materials of this invention are administered, they are most easily and economically used in a dispersed form in an acceptable carrier. When it is said that this material is dispersed, it means that the particles may be molecular in size and held in true solution in a suitable solvent or that the particles may be colloidal in size and dispersed through a liquid phase in the form of a suspension or an emulsion. The term "dispersed" also means that the particles may be mixed with and spread throughout a solid carrier so that the mixture is in the form of a powder or dust. This term is also meant to encompass mixtures which are suitable for use as sprays, including solutions, suspensions or emulsions of the agents of this invention.

In practicing the intranasal route of administration of this invention any practical method can be used to contact the antiviral agent with the respiratory tract of the animal. Effective methods include administration of the agent by intranasal or nasopharyngeal drops and by inhalation as delivered by a nebulizer or an aerosol. Such methods of administration are of practical importance because they provide an easy, safe and efficient method of practicing this invention. For intranasal administration of the agent, usually in an acceptable carrier, a concentration of agent between 1.0 mg/ml and 100 mg/ml is satisfactory. Concentrations in the range of about 30 to 50 mg/ml allow administration of a convenient volume of material.

For topical application the antiviral agents are most conveniently used in an acceptable carrier to permit ease and control of application and better absorption. Here also concentrations in the range of from about 1.0 mg/ml to about 250 mg/ml are satisfactory. In general, in the above two methods of administration a dose within the range of about 1.0 mg/kg to about 250 mg/kg of body weight and, preferably, from about 5.0 mg/kg to about 50 mg/kg of body weight will be administered.

The compounds employed in this invention may be employed alone i.e., without other medicinals, as mixtures of more than one of the herein-described compounds, or in combination with other medicinal agents, such as analgesics, anesthetics, antiseptics, decongestants, antibiotics, vaccines, buffering agents and inorganic salts, to afford desirable pharmacological properties. Further, they may be administered in combination with hyaluronidase to avoid or, at least, to minimize the local irritation and to increase the rate of absorption of the compound. Hyaluronidase levels of at least about 150 (U.S.P.) units are effective in this respect although higher or lower levels can, of course, be used.

Those materials of this invention which are water-insoluble, including those which are of low and/or difficult solubility in water, are, for optimum results, administered in formulations, e.g., suspensions, emulsions, which permit formation of particle sizes of less than about 20μ. The particle sizes of the formulations influence their biological activity apparently through better absorption of the active materials. In formulating these materials various surface active agents and protective colloids are used. Suitable surface active agenst are the partial esters of common fatty acids, such as lauric, oleic, stearic, with hexitol anhydrides derived from sorbitol, and the polyoxyethylene derivatives of such ester products. Such products are sold under the trademarks "Spans" and "Tweens," respectively, and are available from ICI United States Inc., Wilmington, Del. Cellulose ethers, expecially cellulose methyl ether (Methocel, available from the Dow Chemical Co., Midland, Mich.) are highly efficient as protective colloids for use in emulsions containing the materials of this invention.

The water-soluble materials described herein are administered for optimum results in aqueous solution. Typically they are administered in phosphate buffered saline. The water-insoluble compounds are administered in formulations of the type described above or in various other formulations as previously noted. Dimethylsulfoxide serves as a suitable vehicle for water-insoluble compounds. A representative formulation for such compounds comprises formulating 25 to 100 mg of the chosen drug as an emulsion by melting and mixing with equal parts of polysorbate 80 and glycerin to which hot (80° C.) water is added under vigorous mixing. Sodium chloride is added in a concentrated solution to a final concentration of 0.14 M and sodium phosphate, pH 7, is added to a final concentration of 0.01 M to give, for example, the following representative composition.

| | mg/ml |
|---|---|
| Drug | 50.0 |
| Polysorbate 80 | 50.0 |
| Glycerin | 50.0 |
| Sodium Phosphate Monobasic Hydrous | 1.4 |
| Sodium Chloride | 7.9 |
| Water | 842.0 |
| | 1001.3 |

In certain instances, as where clumping of the drug particles occurs, sonication is employed to provide a homogeneous system.

The following examples illustrate the invention but are not to be construed as limiting the same.

EXAMPLE 1

4-(Dichloromethyl)phenoxy acetyl chloride

4-Formylphenoxy acetic acid (3.6 g, 0.02 mole) was added to thionyl chloride (25 ml), and the resulting mixture treated with dimethylformamide (1 drop) and refluxed for 15 minutes. A clear solution was obtained. After evaporation to dryness, the remaining oil was dissolved in 25 ml of methylene chloride and evaporated to dryness three times to remove the dimethylformamide to afford 3.97 g (100% yield) of the acid chloride.

EXAMPLE 2

N,N-Dihexadecyl-4-(dichloromethyl)phenoxy acetamide

Dihexadecylamine (8.88 g, 0.019 mole) was dissolved in a solution of methylene chloride (75 ml) and triethylamine (2.02 g, 0.020 mole). 4-Dichloromethylphenoxy acetyl chloride (3.97 g, 0.02 mole), dissolved in methylene chloride (25 ml), was then added dropwise over a period of 10 minutes, and the resulting clear solution was stirred for 16 hours. The reaction mixture was then washed with water (2×100 ml), saturated sodium bicarbonate solution (2×100 ml) and saturated sodium chloride solution (2×100 ml), dried over sodium sulfate, filtered, and concentrated under vacuum to the desired amide: oil, 10.83 g (92% yield).

EXAMPLE 3

N,N-Dihexadecyl-4-(isonitrosomethyl)phenoxy acetamide

Hydroxylamine hydrochloride (1.26 g, 0.182 mole) was added to a mixture of N,N-dihexadecyl-4-(dichloromethyl)phenoxy acetamide (10.4 g, 0.0164 mole) in water (50 ml), ethanol (80 ml) and tetrahydrofuran (200 ml), and sodium carbonate (0.965 g, 0.0091 mole) in water (20 ml) was added. The mixture was stirred at room temperature (16 hours), concentrated under vacuum to half its volume, diluted with saturated sodium chloride solution (200 ml), and extracted with chloroform (3×150 ml), dried over sodium sulfate, filtered and concentrated under vacuum to give the desired oxime (9.16 g, 88% yield), mp 58°–60° C.

EXAMPLE 4

N,N-Dihexadecyl-4-(aminomethyl)phenoxy acetamide hydrochloride

N,N-Dihexadecyl-4-(isonitrosomethyl)phenoxy acetamide (3.0 g, 0.00467 mole) was dissolved in ethanol (40 ml) saturated with gaseous hydrochloric acid and hydrogenated (50 psi $H_2$, 2 hours) in the presence of 10% palladium on carbon (300 mg). After the reaction was complete, the mixture was filtered and concentrated for crystallization (2.0 g, 64.5% yield), mp 90°–92° C.

The ability of N,N-dihexadecyl-4-(aminomethyl)phenoxy acetamide hydrochloride to induce circulating interferon was determined by mixing the compound with equal weights of polysorbate 80 and glycerol. The mixture was then homogenized in hot 0.14 M NaCl containing 0.01 sodium phosphate, pH 7.

Female Swiss mice (20–25 g body weight) were injected intraperitoneally with an amount of the above diluted emulsion containing 25 mg of the named compound/kg body weight. Blood samples were withdrawn at intervals of 8, 12, 16 and 20 hours after injection. Separated plasma from each sample was serially diluted. L-929 mouse fibroblasts were incubated on microtiter plates with aliquots of the various samples of serially diluted plasma for 18 hours at 37° C. The fibroblast monolayers were then washed with protein-free medium and challenged with 10–40 times the $TCID_{50}$, the dose in which 50% of the cultures are infected, of vesicular stomatitis virus. The virus was allowed to absorb for 1 hour at 37° C. before addition of 0.2 ml of maintenance medium. The cultures were scored and analyzed about 24 to 48 hours later and the plasma interferon level, the reciprocal of the plasma dilution at which 50% of the cultures are protected, determined. The following data were obtained.

| Compound | Plasma Interferon Levels (units/ml) Time (hours after injection) | | | |
|---|---|---|---|---|
| | 8 | 12 | 16 | 20 |
| Ex 4 | 3 | 8 | 16 | 16 |

EXAMPLE 5

N,N-Dihexadecyl-2-[4-(aminomethyl)phenoxy]ethylamine

N,N-Dihexadecyl-4-(aminomethyl)phenoxy acetamide (2.8 g, 0.0042 mole) was dissolved in benzene (30 ml) and treated with sodium bis-(2-methoxyethoxy)-aluminum hydride (5.94 g of a 70% solution in benzene). The mixture was refluxed for 16 hours, cooled and quenched with 10% sodium hydroxide solution (10.2 ml). The organic phase was separated, washed with saturated sodium chloride solution (3×50 ml), dried over sodium sulfate, filtered and concentrated under vacuum to an oil (2.27 g). The product was purified by silica gel chromatography (eluted with a chloroform/ethanol gradient mixture), converted to the hydrochloride salt, and recrystallized from ethanol/acetonitrile (1:1) to give the desired ethyl amine (0.725 g, 25% yield), mp 231°–238° C.

EXAMPLE 6

N,N-Dihexadecyl-4-formylphenoxy acetamide

N,N-Dihexadecyl-4-(dichloromethyl)phenoxy acetamide (39 g, 0.057 mole) was dissolved in methanol (100 ml) and 10 N sodium hydroxide (0.2 ml), refluxed 15 minutes and concentrated under reduced pressure to a solid. The solid was dissolved in chloroform (100 ml), washed with water (2×50 ml) and saturated sodium chloride solution (3×50 ml), dried over sodium sulfate, filtered and concentrated under reduced pressure to give the pure formylphenoxy compound (15 g, 42% yield), mp 39°–42° C.

EXAMPLE 7

N,N-Dihexadecyl-4-(2-hydroxyethylaminomethyl)-phenoxy acetamide

2-Aminoethanol (2.92 g, 0.048 mole) and 5 N methanolic hydrochloric acid (3.2 ml) were dissolved in methanol and cooled (0°–5° C.). A solution of N,N-dihexadecyl-4-formylphenoxy acetamide (5.02 g, 0.008 mole) in tetrahydrofuran (30 ml) was slowly added and the reaction mixture was stirred at room temperature (10 minutes). Sodium cyanoborohydride (0.301 g, 0.0048 mole) was added and the mixture stirred for 7 days. The pH was adjusted to 2.0 with concentrated hydrochloric acid and the mixture then evaporated to dryness. The resulting solid was dissolved in chloroform, washed with water to remove excess ethanolamine, and adjusted with 10 N sodium hydroxide to pH 10. The chloroform layer was then washed with water (3×40 ml) and saturated sodium chloride solution (5×40 ml), dried over sodium sulfate, filtered and concentrated under reduced pressure to an oil (4.0 g). The product was purified by silica gel chromatography (eluted with a benzene/ethanol gradient mixture), converted to the hydrochloride salt, and recrystallized from ethanol (1.41 g, 25% yield), mp 172°–173° C.

EXAMPLES 8-17

In like manner to that described in Examples 1 to 7, the following compounds were prepared using the appropriate amine and substituted phenoxy acetamide:

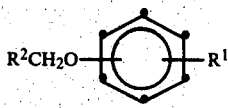

| Example | $R^1$ | $R^2$ | MP(°C.) |
|---|---|---|---|
| 8 | $-CH_2NH_2$ | $4-(C_{18}H_{37})_2NCH_2-$ | 220 |
| 9 | $-CH_2NH_2$ | $4-(C_{14}H_{29})_2NCH_2-$ | 134-138 |
| 10 | $-CH_2NH_2$ | $4-(C_{18}H_{37})_2NCO-$ | 115-119 |
| 11 | $-CH_2NH_2$ | $4-(C_{14}H_{29})_2NCO-$ | 160-166 |
| 12 | $-CH_2NH_2$ | $2-(C_{16}H_{33})_2NCO-$ | 70-75 |
| 13 | $-CH_2NHC_2H_5$ | $4-(C_{16}H_{33})_2NCO-$ | 114-116 |
| 14 | $-CH_2N(CH_2CH_2OH)_2$ | $4-(C_{16}H_{33})_2NCO-$ | 213-215 |
| 15 | $-CH_2N(C_2H_5)_2$ | $4-(C_{14}H_{29})_2NCO-$ | 82-85 |
| 16 | $-CH_2NH_2$ | $3-(C_{16}H_{33})_2NCO-$ | 118-119 |
| 17 | $-CH_2NH_2$ | $3-(C_{16}H_{33})_2NCH_2-$ | 90-95 |

EXAMPLE 18

The antiviral activity was determined for the compounds listed below.

Three groups of 10 female albino mice (20-25 g body weight) were given single 0.5 ml intraperitoneal injections containing dosage levels ranging from 0.5-125 mg of the named compound/kg body weight, respectively. A fifth control group was given no such injection. Eighteen to 24 hours after injection all five groups were challenged with a 0.2 ml subcutaneous injection containing 20-30 times the $LD_{50}$, the dosage level causing a 50% death rate in 10 days from encephalomycarditis virus.

Antiviral activity is expressed as the relative survival ($S_r$) in experimental groups compared to the controls on the tenth day after challenge. Most tests were performed in duplicate.

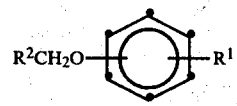

| Example No. | $R^1$ | $R^2$ | mg/kg | $S_r$ | |
|---|---|---|---|---|---|
| 4 | $-CH_2NH_2$ | $4-(C_{16}H_{33})_2NCO-$ | 125 | 91 | 97 |
| | | | 25 | 73 | 97 |
| | | | 5 | 63 | 88 |
| | | | 1 | 19 | 0 |
| 5 | $-CH_2NH_2$ | $4-(C_{16}H_{33})_2NCH_2-$ | 125 | 91 | 74 |
| | | | 25 | 91 | 87 |
| | | | 5 | 81 | 58 |
| | | | 1 | 31 | 10 |
| 7 | $-CH_2NHCH_2CH_2OH$ | $4-(C_{16}H_{33})_2NCO-$ | 15 | 30 | 61 |
| | | | 5 | 58 | 70 |
| | | | 1.5 | 45 | 30 |
| | | | 0.5 | 0 | 11 |
| 8 | $-CH_2NH_2$ | $4-(C_{18}H_{37})_2NCH_2-$ | 50 | 80 | 100 |
| | | | 15 | 59 | 88 |
| | | | 5 | 48 | 32 |
| | | | 1.5 | 20 | 31 |
| 9 | $-CH_2NH_2$ | $4-(C_{14}H_{29})_2NCH_2$ | 15 | 44 | |
| | | | 5 | 56 | |
| | | | 1.5 | 11 | |
| | | | 0.5 | 0 | |
| 10 | $-CH_2NH_2$ | $4-(C_{18}H_{37})_2NCO-$ | 125 | 78 | 78 |
| | | | 25 | 100 | 91 |
| | | | 5 | 71 | 43 |
| | | | 1 | 0 | 0 |
| 11 | $-CH_2NH_2$ | $4-(C_{14}H_{29})_2NCO-$ | 125 | 100 | 100 |
| | | | 25 | 83 | 78 |
| | | | 5 | 60 | 96 |
| | | | 1 | 0 | 14 |
| 12 | $-CH_2NH_2$ | $2-(C_{16}H_{33})_2NCO-$ | 15 | 38 | 70 |
| | | | 5 | 38 | 30 |
| | | | 1.5 | 1 | 12 |
| | | | 0.5 | 0 | 21 |
| 13 | $-CH_2NHC_2H_5$ | $4-(C_{16}H_{33})_2NCO-$ | 15 | 47 | |
| | | | 5 | 43 | |
| | | | 1.5 | 4 | |
| | | | 0.5 | 8 | |
| 14 | $-CH_2N(CH_2CH_2OH)_2$ | $4-(C_{16}H_{33})_2NCO-$ | 15 | 67 | 50 |
| | | | 5 | 37 | 48 |
| | | | 1.5 | 11 | 5 |
| | | | 0.5 | 0 | 0 |
| 15 | $-CH_2N(C_2H_5)_2$ | $4-(C_{14}H_{29})_2NCO-$ | 15 | 55 | 35 |
| | | | 5 | 31 | 22 |
| | | | 1.5 | 11 | 11 |
| | | | 0.5 | 11 | 13 |
| 16 | $-CH_2NH_2$ | $3-(C_{16}H_{33})_2NCO-$ | 50 | 91 | 89 |

-continued

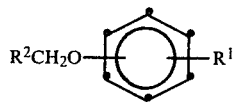

| Example No. | $R^1$ | $R^2$ | mg/kg | $S_r$ | |
|---|---|---|---|---|---|
| | | | 15 | 80 | 92 |
| | | | 5 | 52 | 45 |
| | | | 1.5 | 1 | 1 |
| 17 | —$CH_2NH_2$ | 3-$(C_{16}H_{33})_2NCH_2$ | 15 | 91 | 91 |
| | | | 5 | 100 | 57 |
| | | | 1.5 | 52 | 26 |
| | | | 0.5 | 22 | 14 |

EXAMPLE 19

Correlation between number of carbon atoms in alkyl groups ($R^2$) and antiviral activity is shown in the following table:

| | $R^2CH_2O$—$C_6H_4$—$R^1$ | | |
|---|---|---|---|
| $R^1$ | $R^2$ | mg/kg[a] | $S_r{}^b$ |
| —$CH_2NH_2{}^c$ | 4-$(C_{10}H_{21})_2NCO$ | 15 | 2 |
| | | 5 | 6 |
| | | 1.5 | 2 |
| | | 0.5 | 2 |
| —$CH_2NH_2{}^d$ | 4-$(C_{10}H_{21})_2NCH_2$ | 15 | 22 |
| | | 5 | 22 |
| | | 1.5 | 14 |
| | | 0.5 | 7 |
| —$CH_2NH_2$ | 4-$(C_{16}H_{33})_2NCO$— | 125 | 94 |
| | | 25 | 85 |
| | | 5 | 76 |
| | | 1 | 10 |
| —$CH_2NH_2$ | 4-$(C_{16}H_{33})_2NCH_2$— | 125 | 82 |
| | | 25 | 89 |
| | | 5 | 70 |
| | | 1 | 20 |

[a]Compounds formulated in aqueous polysorbate 80 and glycerol and administered intraperitoneally.
[b]An $S_r$ value must be 30 or greater to be considered significant.
[c]Compound was an oil as the HCl salt.
[d]Compound was a waxy solid as the HCl salt; m.p. 124-9° C.

It has been found that compounds with alkyl groups containing 10 or less carbon atoms lack antiviral activity. It has also been found that these compounds with lower alkyl groups cannot be tested in mice at levels as high as 125 mg/kg because death occurs in less than 12 hours.

Compounds described in U.S. Pat. No. 3,047,628 are related compounds with alkyl groups containing 10 or less carbon atoms. Thus, they can be expected to lack antiviral activity and to exhibit undesirable toxicity.

The dialkoxybenzyl amines of U.S. Pat. No. 3,960,958 are structurally unrelated to the monoamidoalkoxy- and monoaminoalkoxybenzyl amines of the present invention.

What is claimed is:
1. A compound of the formula

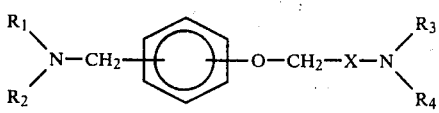

and the non-toxic acid addition salts thereof wherein
$R_1$ is hydrogen, lower alkyl or lower hydroxyalkyl;
$R_2$ is hydrogen or lower hydroxyalkyl;
$R_3$ is hydrocarbyl containing 14 to 18 carbon atoms;
$R_4$ is hydrocarbyl containing 14 to 18 carbon atoms; and X is —CO— or —$CH_2$—.

2. A compound of claim 1 wherein $R_3$ and $R_4$ are normal alkyl.

3. A compound of claim 1 wherein $R_3$ and $R_4$ have an equal number of carbon atoms.

4. A compound of claim 1 wherein $R_3$ and $R_4$ are n-hexadecyl.

5. A compound of claim 1 wherein $R_3$ and $R_4$ are n-octadecyl.

6. A compound of claim 1 wherein the benzene ring of said structure is para substituted.

7. A compound of claim 1 wherein the benzene ring of said structure is meta substituted.

8. A compound of claim 1 wherein $R_3$ and $R_4$ are n-hexadecyl and the benzene ring of said structure is para substituted.

9. A compound of claim 1 wherein $R_3$ and $R_4$ are n-hexadecyl and the benzene ring of said structure is meta substituted.

10. A compound of claim 8 wherein $R_1$ and $R_2$ are hydrogen.

11. A compound of claim 9 wherein $R_1$ and $R_2$ are hydrogen.

12. A process for combating viral infections in vertebrates comprising the parenteral, intranasal or topical administration of an antivirally effective amount of a compound of claim 1.

* * * * *